US012728250B2

(12) United States Patent
Balko

(10) Patent No.: US 12,728,250 B2
(45) Date of Patent: Sep. 8, 2026

(54) SYSTEMS FOR TRANSCAROTID ARTERY REVASCULARIZATION

(71) Applicant: TAHOE MEDICAL, L.P., Menlo Park, CA (US)

(72) Inventor: Ryan Balko, Menlo Park, CA (US)

(73) Assignee: TAHOE MEDICAL, L.P., Menlo Park, CA (US)

( * ) Notice: Subject to any disclaimer, the term of this patent is extended or adjusted under 35 U.S.C. 154(b) by 0 days.

(21) Appl. No.: 19/277,667

(22) Filed: Jul. 23, 2025

(65) Prior Publication Data

US 2026/0166294 A1 Jun. 18, 2026

Related U.S. Application Data

(60) Provisional application No. 63/674,516, filed on Jul. 23, 2024.

(51) Int. Cl.

| | |
|---|---|
| ***A61M 39/06*** | (2006.01) |
| ***A61F 2/95*** | (2013.01) |
| ***A61M 25/00*** | (2006.01) |
| ***A61M 25/06*** | (2006.01) |
| ***A61M 29/00*** | (2006.01) |

(Continued)

(52) U.S. Cl.

CPC ........... *A61M 39/0693* (2013.01); *A61F 2/95* (2013.01); *A61M 29/00* (2013.01); *A61M 25/0045* (2013.01); *A61M 25/005* (2013.01); *A61M 2025/0681* (2013.01); *A61M 2025/09183* (2013.01); *A61M 2039/0258* (2013.01);

(Continued)

(58) Field of Classification Search

CPC .............. A61M 39/0693; A61M 29/00; A61M 25/0045; A61M 25/005; A61M 2025/0681; A61M 2025/09183; A61M 2039/0258; A61M 2039/0273; A61M 2205/0266; A61M 39/00; A61M 2039/0653; A61M 2039/0646; A61M 2039/064; A61M 2039/0633; A61M 39/06; A61M 25/00; A61F 2/95

See application file for complete search history.

(56) References Cited

U.S. PATENT DOCUMENTS 6,592,544 B1 * 7/2003 Mooney ................ A61M 39/24
604/35
6,902,540 B2 6/2005 Dorros et al.

(Continued)

FOREIGN PATENT DOCUMENTS

WO WO-2012021406 2/2012
WO WO-2012032698 3/2012

(Continued)

OTHER PUBLICATIONS

Boston Scientific., "WALLSTENT™ Endoprosthesis Proven Solution, Dependable Choice", (2020). (4 pages).

(Continued)

*Primary Examiner* — Rebecca E Eisenberg
*Assistant Examiner* — Alessandro R Del Priore
(74) *Attorney, Agent, or Firm* — McDermott Will & Schulte LLP

(57) ABSTRACT

A system for neuroprotection for use during carotid interventions comprising an arterial access devices comprising an arterial sheath and an extension device removably connected to the proximal end of the arterial sheath.

28 Claims, 14 Drawing Sheets

(51) Int. Cl.
*A61M 39/02* (2006.01)
*A61M 25/09* (2006.01)

(52) U.S. Cl.
CPC ............... *A61M 2039/0273* (2013.01); *A61M 2205/0266* (2013.01)

(56) References Cited

U.S. PATENT DOCUMENTS

| | | | | |
|---|---|---|---|---|
| 7,172,621 | B2 | 2/2007 | Theron | |
| 7,323,006 | B2 | 1/2008 | Andreas et al. | |
| 8,002,728 | B2 | 8/2011 | Chang | |
| 8,157,760 | B2 | 4/2012 | Criado et al. | |
| 8,343,089 | B2 | 1/2013 | Chang | |
| 8,414,516 | B2 | 4/2013 | Chang | |
| 8,545,432 | B2 | 10/2013 | Renati et al. | |
| 8,858,490 | B2 | 10/2014 | Chou et al. | |
| 8,870,805 | B2 | 10/2014 | Chang | |
| 9,011,364 | B2 | 4/2015 | Criado et al. | |
| 9,084,857 | B2 | 7/2015 | Cully et al. | |
| 9,126,018 | B1 | 9/2015 | Garrison | |
| 9,241,699 | B1 | 1/2016 | Kume et al. | |
| 9,259,215 | B2 | 2/2016 | Chou et al. | |
| 9,399,118 | B2 | 7/2016 | Kume et al. | |
| 9,655,755 | B2 | 5/2017 | Chou et al. | |
| 9,662,118 | B2 | 5/2017 | Chang | |
| 9,662,480 | B2 | 5/2017 | Kume et al. | |
| 9,669,191 | B2 | 6/2017 | Chou et al. | |
| 9,789,242 | B2 | 10/2017 | Criado et al. | |
| 9,820,761 | B2 | 11/2017 | Garrison et al. | |
| 10,039,906 | B2 | 8/2018 | Kume et al. | |
| 10,085,864 | B2 | 10/2018 | Chou et al. | |
| 10,226,598 | B2 | 3/2019 | Chou et al. | |
| 10,238,853 | B2 | 3/2019 | Kume et al. | |
| 10,286,139 | B2 | 5/2019 | Criado et al. | |
| 10,426,885 | B2 | 10/2019 | Criado et al. | |
| 10,543,307 | B2 | 1/2020 | Criado et al. | |
| 10,709,832 | B2 | 7/2020 | Criado et al. | |
| 10,722,239 | B2 | 7/2020 | Chang | |
| 10,799,244 | B2 | 10/2020 | Cully et al. | |
| 10,864,357 | B2 | 12/2020 | Kume et al. | |
| 10,952,882 | B2 | 3/2021 | Chou et al. | |
| 11,364,332 | B2 | 6/2022 | Criado et al. | |
| 11,759,613 | B2 | 9/2023 | Kume et al. | |
| 2011/0034986 | A1* | 2/2011 | Chou | A61F 2/844 604/9 |
| 2014/0074037 | A1* | 3/2014 | Bornhoft | A61M 25/02 604/180 |
| 2019/0275288 | A1* | 9/2019 | Kizuka | A61M 25/0054 |
| 2020/0155743 | A1* | 5/2020 | Siess | A61M 25/1002 |
| 2023/0225749 | A1 | 7/2023 | Stratton et al. | |
| 2024/0293655 | A1* | 9/2024 | Hong | A61M 39/0247 |

FOREIGN PATENT DOCUMENTS

| | | |
|---|---|---|
| WO | WO-2017058818 | 4/2017 |
| WO | WO-2023101982 | 6/2023 |

OTHER PUBLICATIONS

Idev Technologies, Inc. (2007). SUPERATM Interwoven Self-Expanding Nitinol Biliary Stent Delivery Catheter (6 pages).

Silk Road Medical. (2023). Instructions for Use ENROUTE® Transcarotid Neuroprotection System (NPS) (20 pages).

* cited by examiner

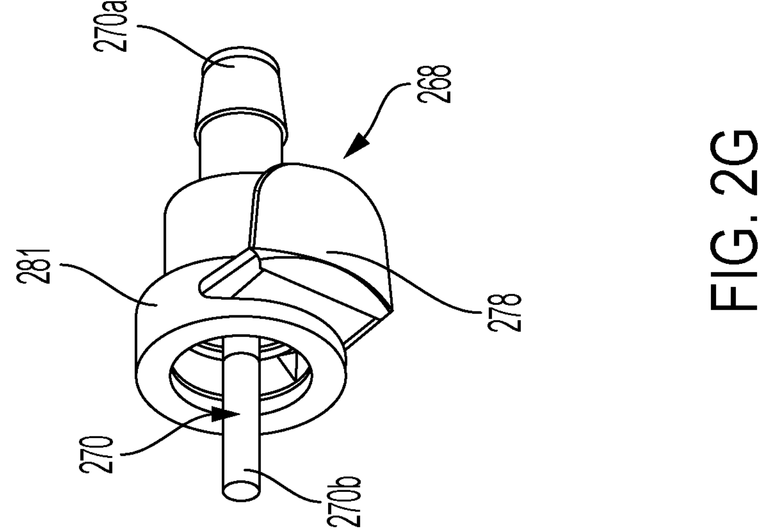
FIG. 2G
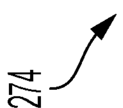

310
350
306
304

304
302a
330
302

300
310
302b
312

420
422b
422c
422a 419
404
418
SEE FIG. 4C

SYSTEMS FOR TRANSCAROTID ARTERY REVASCULARIZATION

CROSS-REFERENCE TO RELATED APPLICATIONS

This application claims priority to and the benefit of U.S. Provisional Patent Application No. 63/674,516, filed on Jul. 23, 2024, and entitled "SYSTEMS FOR TRANSCAROTID ARTERY REVASCULARIZATION", the entire contents of the above-referenced application is hereby incorporated herein by reference.

FIELD

The technologies described in this specification relate to systems for vascular interventions.

BACKGROUND

The carotid arteries are arteries that supply the head and neck with oxygenated blood. Carotid artery disease occurs when fatty deposits called plaques are deposited on the carotid arteries. The deposition of plaque on the carotid arteries can narrow the junction between the common carotid artery (located in the neck) and the internal carotid artery, restricting blood flow to the brain. Restriction of blood flow to the brain increases the risk of transient ischemic attacks, ischemic stroke, or death.

To repair blockages in the carotid artery caused by the accumulation of plaque, various treatment options are available. The treatment options include surgical interventions, such as carotid endarterectomy or angioplasty, including the placement of a stent to prevent narrowing of the carotid arteries. Surgical interventions (e.g., revascularization) are highly invasive procedures which present issues such as infection risk and significant recovery time for the patient.

Transcarotid Artery Revascularization (TCAR) is a minimally invasive procedure to repair a damaged or blocked carotid artery. During the TCAR procedure, blood flow in the artery is temporarily reversed away from the brain and the blood is filtered to remove any plaque particles before returning it back to the patient's vein. The TCAR procedure can also involve steps including stabilization of the plaque on the artery walls via a balloon and the placement of a stent to hold the artery open.

To ensure the success and efficiency of the TCAR procedure, there is a need for a TCAR system capable of being convenient for the surgeon to perform the TCAR procedure with, achieve sufficient retrograde flow (i.e., control the rate of blood flow away from the carotid arteries), filter the blood of plaque particles sufficiently, reduce risk of procedural and post-procedural emboli, improve the level of hemostasis, and allow for concurrent procedures, such as cardiac stenting and angioplasty, if necessary.

SUMMARY

Disclosed in this specification are technologies including systems and methods for addressing various problems and shortcomings of the state of the art, as identified above. More particularly, disclosed herein are systems and methods for transcarotid artery revascularization.

According to a first aspect of the present disclosure, there is provided a system for transcarotid artery revascularization comprising an arterial access devices comprising an arterial sheath and an extension device. The arterial sheath comprises a first body having a proximal end, a distal end, a first lumen, and a first hemostatic valve positioned at the proximal end, and a first lock portion having a proximal end, a distal end, and a lock lumen, the first lock portion extending proximally from the proximal end of the first body, the lock lumen separated from the first lumen by the first hemostatic valve. The extension device comprises a second body having a proximal end, a distal end, a second lumen, and a second hemostatic valve positioned at the proximal end of the extension device, a second lock portion having a proximal end, a distal end, the second lock portion extending distally from the distal end of the second body, the second lock portion configured to releasably interlock with the first lock portion, and a defeater at least partially disposed inside the second body, the defeater having a proximal end, a distal end, and a defeater lumen extending distally from a distal end of the second lumen, the defeater configured to actuate the first hemostatic valve such that, when the extension device is connected to the arterial sheath, the first lumen, the defeater lumen, and the second lumen form a continuous lumen.

BRIEF DESCRIPTION OF THE DRAWINGS

For clarity and understanding, some implementations of the technologies are described in more detail in the appended drawings. These drawings should not, however, be considered as limiting the scope of the inventions and the inventions include any number of other equally useful implementations.

FIG. 2G shows a perspective view of an exemplary implementation of an arterial connector of a TCAR system as described in this specification.

DETAILED DESCRIPTION

Figure 1:
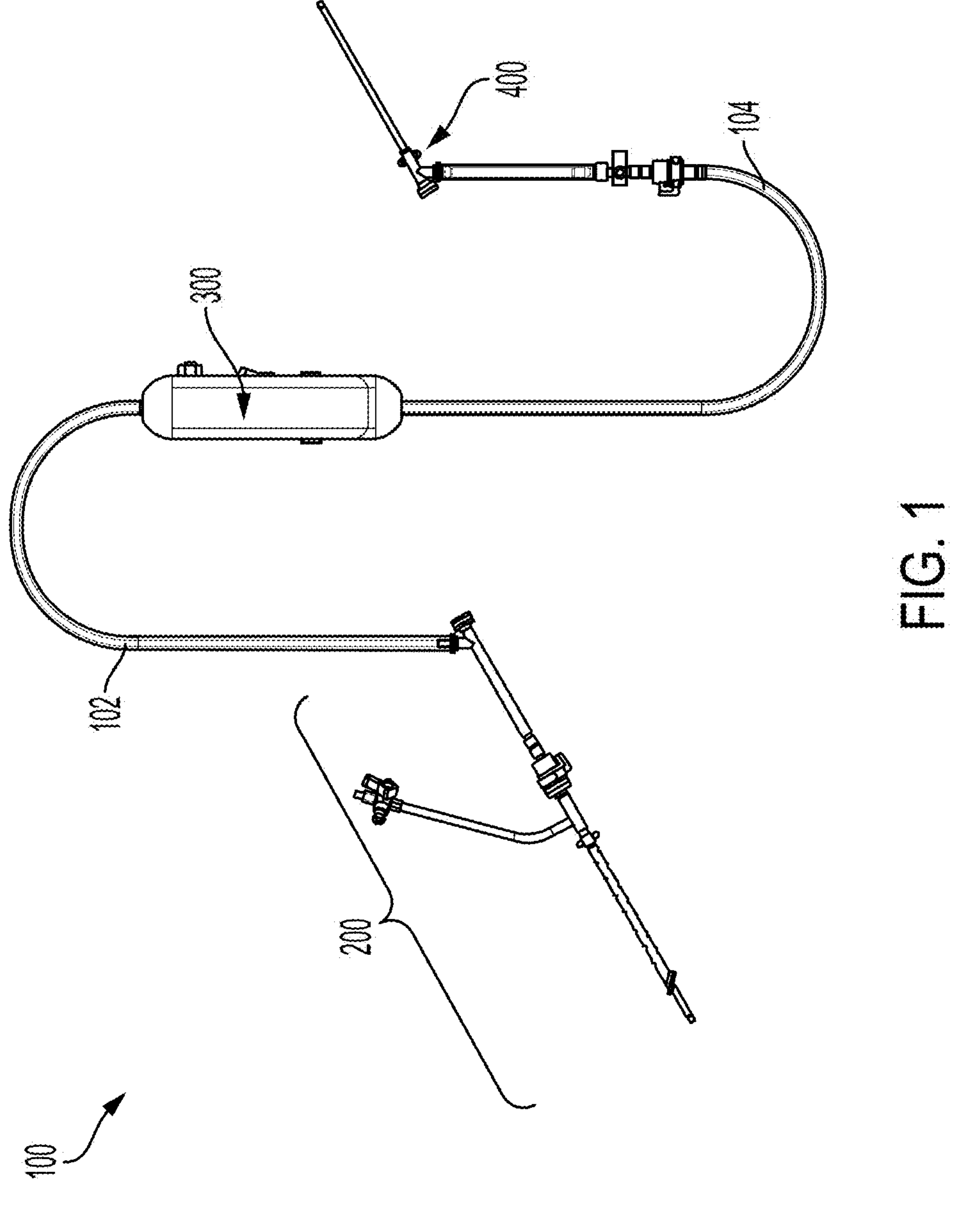
FIG. 1 shows a side view of an exemplary TCAR system as described in this specification.

Referring to the drawings, FIG. 1 shows an exemplary TCAR system 100 as described in this specification. FIG. 1 also presents the primary structural components of the TCAR system 100. These include an arterial access device 200 and a venous sheath 400 connected to each other via a flow controller 300. The arterial access device 200 is fluidically connected to the flow controller 300 via at least one arterial flow tubing 102. The venous sheath 400 is fluidically connected to the flow controller 300 via at least one venous flow tubing 104. The TCAR system 100 of FIG. 1 can be used by a surgeon to treat a damaged or blocked carotid artery as described above.

Figure 2A:
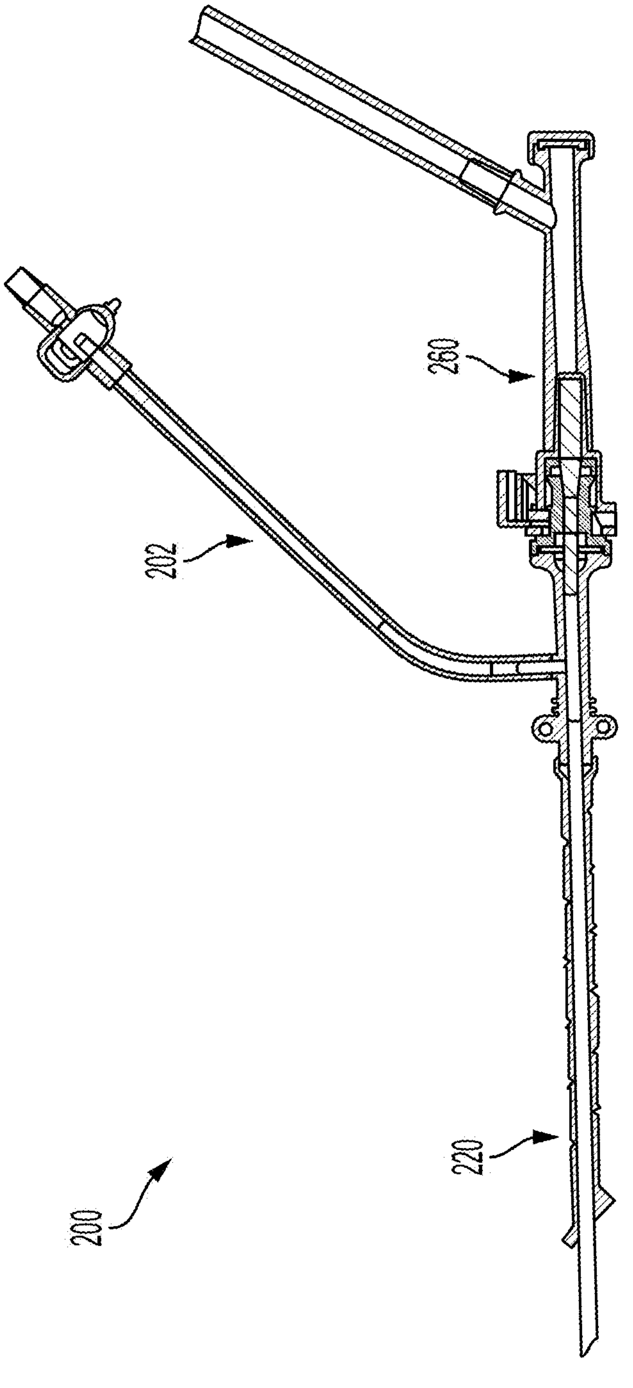
FIG. 2A shows a cross-sectional view of an exemplary implementation of an arterial access device of a TCAR system as described in this specification.

Referring to FIG. 2A, a cross-sectional view of an exemplary implementation of an arterial access device 200 of a TCAR system 100 is shown. In the implementation of the arterial access device 200 presented in FIG. 2A, the arterial access device 200 includes an arterial sheath 220 and an extension device 260 mechanically and fluidically connected to each other. The arterial sheath 220 is configured to be inserted into the carotid artery through an open surgical incision in neck below the carotid bifurcation during the TCAR procedure. The arterial sheath 220 is also configured allow blood flow from the carotid artery to the flow controller 300 via the extension device 260 and the at least one arterial flow tubing 102. In some implementations, the arterial sheath 220 can be configured to allow the insertion of a stent and/or a cardiac balloon (e.g., as used in angioplasty procedures). In the implementation of the arterial access device 200 shown in FIG. 2A, the arterial access device 200 further includes a branching tube 202 disposed on and fluidically connected to the arterial sheath 220. In some implementations, the branching tube 202 can be configured to allow the flow of medicaments into the blood flow from the carotid artery or to allow for insertion of one or more medical devices.

Figures 2B, 2C:
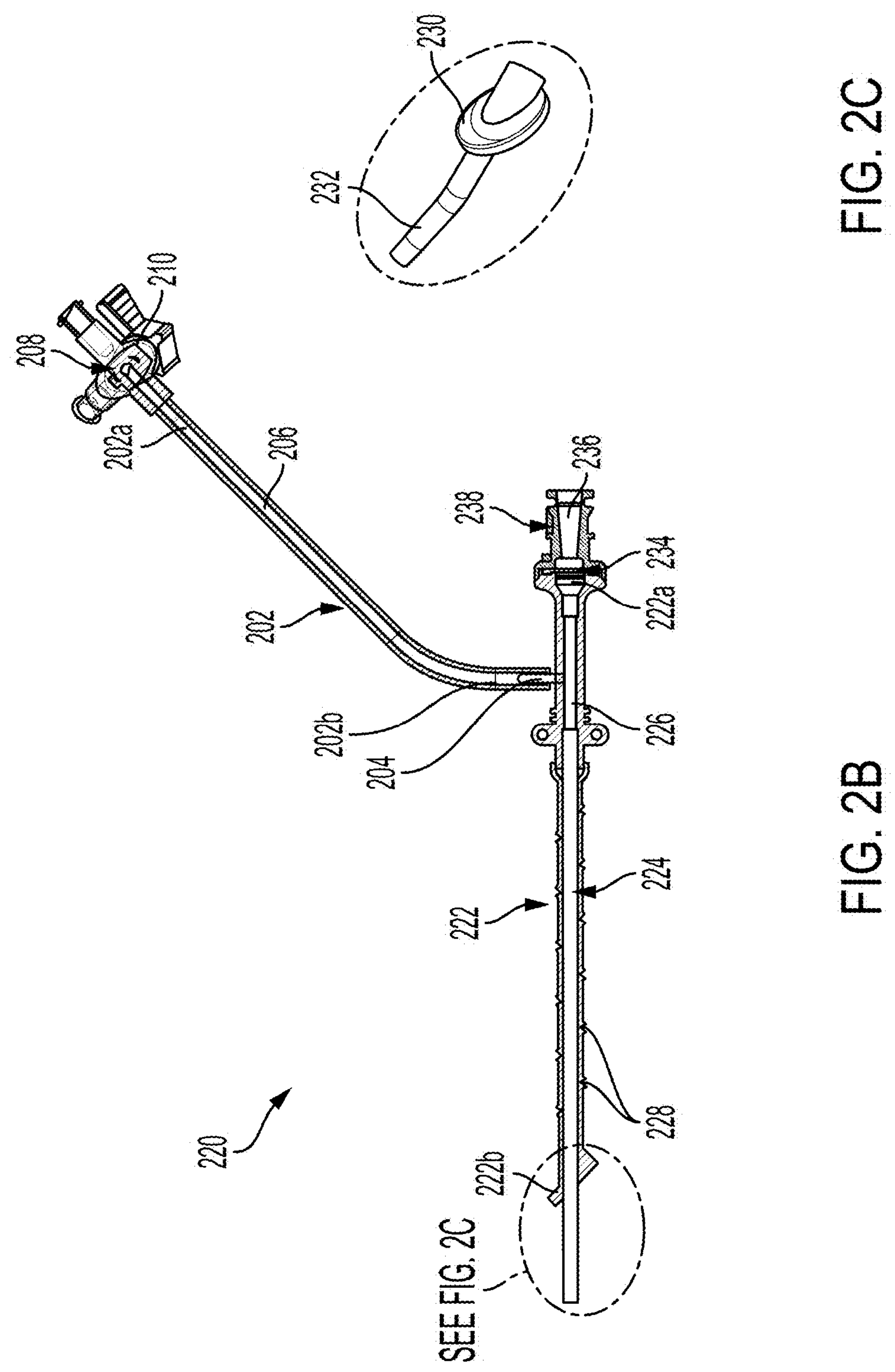
FIG. 2B shows cross-sectional view of an exemplary implementation of an arterial sheath of a TCAR system as described in this specification.
FIG. 2C shows a perspective view of a distal end of the first body of the arterial sheath of FIG. 2B as described in this specification.

Referring to FIG. 2B, a cross-sectional view of an exemplary implementation of an arterial sheath 220 of the arterial access device 200 of FIG. 2A is shown. The implementation of the arterial sheath 220 presented in FIG. 2B includes a (first) body 222 comprising a proximal end 222*a*, a distal end 222*b*, a lumen 226, and a (first) hemostatic valve 234 positioned at the proximal end 222*a*. The (first) hemostatic valve 234 can be configured to prevent leaking of the blood from the lumen 226 and prevent air from entering the arterial sheath 220 during the TCAR procedure.

In some implementations of the arterial sheath 220, the arterial sheath 220 can further include an inner tube 224, at least partially disposed in the (first) body 222 of the arterial sheath 220, forming a part of the lumen 226 of the arterial sheath 220. In this implementation presented in FIG. 2B, a distal end of the inner tube 224 can be configured to be inserted into the carotid artery and a proximal end of the inner tube 224 can be connected to the (first) lumen 226 of the arterial sheath 220. In some implementations of the arterial sheath 220, as shown in FIG. 2B, the (first) body 222 of the arterial sheath 220 can include a plurality of notches, ridges, or fenestrations 228 configured to provide the surgeon flexibility to secure the arterial sheath 220 to the patient tissue regardless of patient anatomy. The notches, ridges, and/or fenestrations 228 can be spaced at certain (fixed or variable) intervals along the length of the arterial sheath 220, providing means for securing the arterial sheath 220 at various depth of penetration into the patient tissue.

Referring to FIG. 2C, a perspective view of the distal end 222*b* of the first body 222 is shown. In some implementations, like the implementation of FIGS. 2B and 2C, the distal end 222*b* of the (first) body 222 can also include a foot plate 230 configured to seal the insertion point in the carotid artery to prevent blood loss when inner tube is inserted into the carotid artery. In some implementations, a distal end of the inner tube 224 can comprise a flexible tip 232 configured to bend in a bending angle between 00 and 900, e.g., between 0° and 30°. In some implementations, a distal end of the inner tube 224 can comprise a flexible tip 232 configured to bend in a bending angle of about 20°.

The implementation of the arterial sheath 220 presented in FIG. 2B includes a first lock portion 238 extending proximally from the proximal end 222*a* of the (first) body 222 of the arterial sheath 220 and separated from the body of the arterial sheath 220 by the (first) hemostatic valve 234. The first lock portion 238 comprises a proximal end, a distal end, and a lock lumen 236 fluidically connected to the (first) lumen 226 of the (first) body 222 of the arterial sheath 220. In some implementations of the arterial sheath 220, the lock portion 238 can be configured to connect the extension device 260 with the arterial sheath 220 via the lock lumen 236. In some implementations, the lock lumen 238 comprises a frustoconical portion, e.g., to facilitate insertion of the extension device 260.

In some implementations of the arterial sheath 220, such as the implementation presented in FIG. 2B, the arterial sheath 220 can include a branching tube 202 disposed on the (first) body 222 of the arterial sheath 220. In the implementation shown in FIG. 2B, the branching tube 202 comprises a proximal end 202*a*, a stopcock subassembly valve 208 comprising a stop switch 210 disposed on the proximal end 202*a*, and a distal end 202*b* attached to the (first) body 222 of the arterial sheath 220. The distal end 202*b* of the branching tube 202 is connected to the (first) body 222 of the arterial sheath 220 such that a branching lumen 206 of the branching tube 202 is in fluid communication with the lumen 226 of the arterial sheath 220. In this implementation, the distal end 202*b* of the branching tube 202 forms a (first) lateral opening 204 in the lumen 226 of the arterial sheath 220. In some implementations, the lateral opening 204 is positioned between the proximal end of the inner tube 224 and the hemostatic valve 234 of the arterial sheath 220. In some implementations, the branching tube 202 can be used, e.g., to flow medicaments into the blood flow from the carotid artery or to allow for insertion of one or more medical devices.

Figures 2D, 2E:
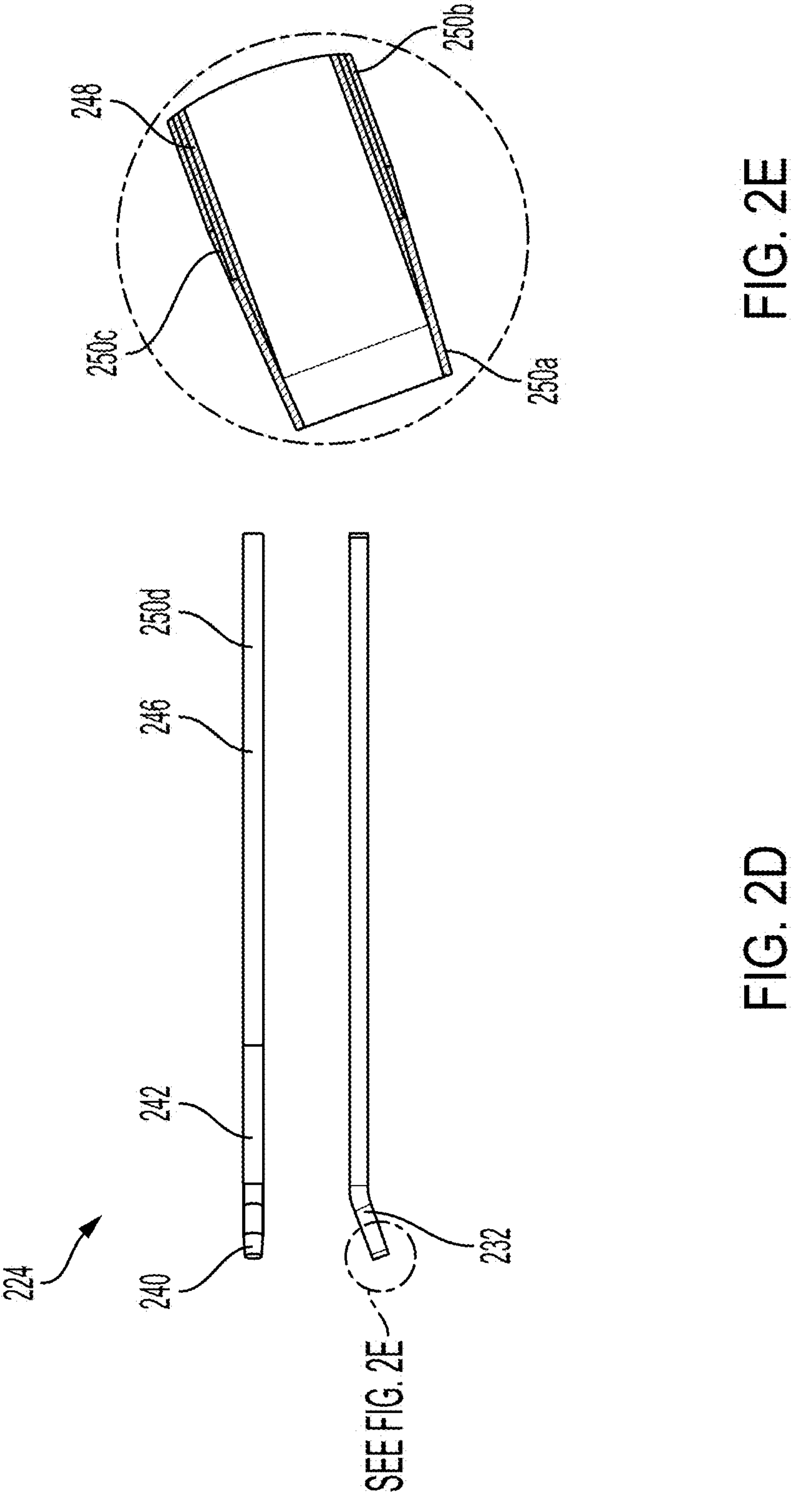
FIG. 2D shows a side view and a top view of the distal end of an exemplary implementation of an inner tube of the arterial sheath presented in FIG. 2B.
FIG. 2E shows a cross-sectional view of the distal end of an exemplary implementation of the inner tube of the arterial sheath presented in FIG. 2B.

Referring to FIG. 2D, a side view and a top view of the distal end of an exemplary implementation of the inner tube 224 of the arterial sheath 220 presented in FIG. 2B are shown. The inner tube presented in FIG. 2D can be composed of three segments: segment A 240, segment B 242, and segment C 246.

Referring to FIG. 2E, a cross-sectional view of the distal end of the exemplary implementation of the (first) inner tube 224 of the arterial sheath 220 presented in FIG. 2B. In the implementation presented in FIG. 2E, the (first) inner tube 224 comprises a liner 248 forming an innermost layer of the at least a part of the inner tube 224 in the segments A 240, B 242, and C 246. In some implementations, the liner 248 is made of a polymer material, e.g., comprising polytetrafluoroethylene (PTFE), and extends from the proximal end of the inner tube 224 to a point about 1-3 mm from the distal end. In some implementations, the inner tube 224 comprises a coiled wire 250*c* forming a layer around the liner 248. In some implementations, coiled wire 250*c* is made of a metal and extends from the proximal end of the inner tube 224 to a point about 2-5 mm from the distal end. The coiled wire 250*c* and/or liner 248 are coated with a polymer material. In an example segment A 240, the liner 248 extends distally from the distal end of the coiled wire 250*c*. The coiled wire 250*c* and the liner 248 are coated with a first material forming a first layer 250*a*. In an example implementation, segment A 240 is between 2 and 8 mm, e.g., about 4-5 mm in length. In some implementations, the first layer 250*a* (alone) forms the distal-most tip of the inner tube 224. In an example segment B 242, proximal to segment A 240, the coiled wire 250*c* is coated with a second material forming a second layer 250*b* contiguous with the first layer 250*a*. In an example implementation, segment B 242 is between about 30 and 40 mm, e.g., about 35 mm in length. In an example segment C 248, proximal to segment B 242, the coiled wire 250*c* is coated with a third material a third layer 250*d* contiguous with the second layer 250*b*. In an example implementation, segment C 246 is between about 80 and 100 mm, e.g., about 95 mm in length. The third material can be stiffer than the first material or second material. In some implementations, the first material is a 63D Pebax, the second material is a 35D Pebax, a coil material of the coiled wire 250*c* is a 0.004" coiled round wire, and the third material is a 55D Pellethane.

Figure 2F:
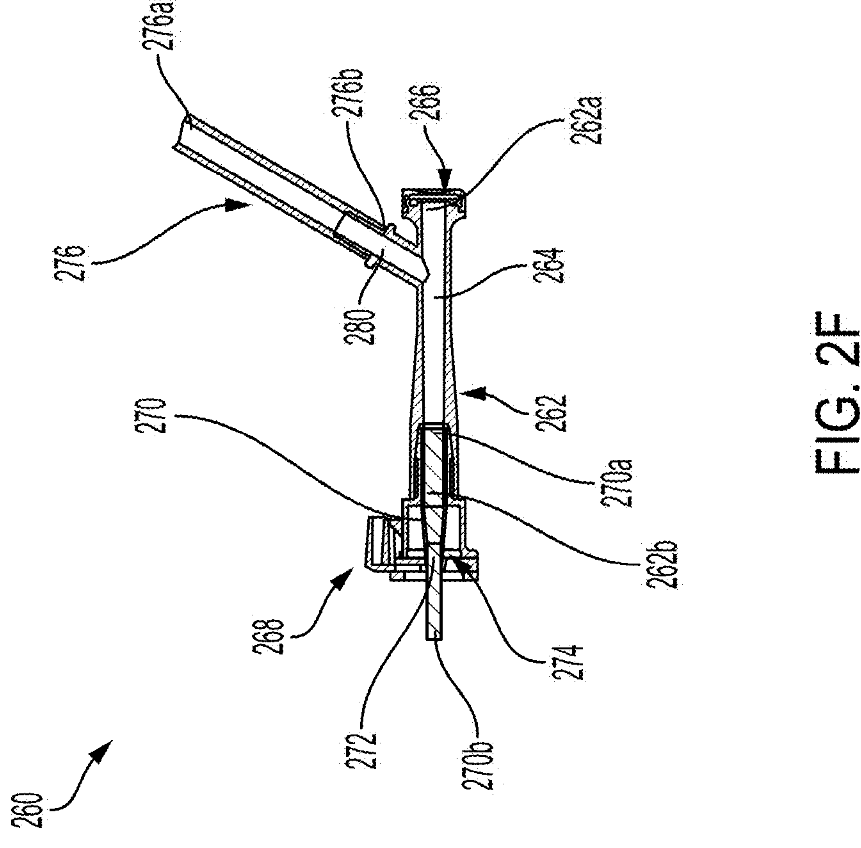
FIG. 2F shows a cross-sectional view of an exemplary implementation of an extension device of a TCAR system as described in this specification.

Referring to FIG. 2F, a cross-sectional view of an exemplary implementation of an extension device 260 of the arterial access device 200 is shown. The implementation of the extension device 260 presented in FIG. 2F includes a (second) body 262 having a proximal end 262*a*, a distal end 262*b*, a lumen 264, and a (second) hemostatic valve 266 positioned at the proximal end of the extension device 260. The hemostatic valve 266 can be configured to prevent leaking of the blood from the lumen 264 of the extension device 260 and prevent air from entering the extension device 260 during the TCAR procedure.

The implementation of the extension device 260 presented in FIG. 2F includes a (second) lock portion 268 having a proximal end and a distal end. In this implementation, the lock portion 268 of the extension device 260 extends distally from the distal end 262*b* of the body 262 of the extension device 260 and is configured to releasably interlock the lock portion 268 of the extension device 260 with the lock portion 268 of the arterial sheath 220.

In the implementation of extension device 260 presented in FIG. 2F, the extension device 260 further includes a defeater 270 partially disposed on/in the body of the extension device 260. In this implementation, the defeater 270 comprises a proximal portion 270*a*, a distal portion 270*b*, a defeater lumen 272, where the defeater lumen 272 is configured to extend distally from a distal end of lock portion 268. In some implementations, including the implementation of FIG. 2F, the defeater 270 can be configured to actuate the hemostatic valve 234 of the arterial sheath 220 (shown in FIG. 2B), e.g., by piercing a diaphragm in the hemostatic valve 234, such that when the extension device 260 is connected to the arterial sheath 220, the lumen 226 of the arterial sheath 220, the defeater lumen 272, and the lumen 264 of the extension device 260 form a continuous lumen of the arterial access device 200.

In some implementations of the extension device 260, such as the implementation presented in FIG. 2D, the extension device 260 can include a (second) branching tube 276 attached to the body 262 of the extension device 260. In the implementation shown in FIG. 2F, the branching tube 276 comprises a proximal end 276*a* and a distal end 276*b* attached to the body 262 of the extension device 260. In this implementation, the distal end 276*b* of the branching tube 276 is connected to the body 262 of the extension device 260 such that a branching lumen 278 of the branching tube 276 is in fluid communication with the lumen 264 of the extension device 260. In this implementation, the distal end 276*b* of the branch tube 276 forms a lateral opening 280 in the lumen 264 of the extension device 260. In some implementations, the lateral opening 280 is positioned between the defeater 270 and the (second) hemostatic valve 266 of the extension device 260. Optionally, a hemostatic cap (not shown in FIG. 2F) can be coupled to the hemostatic valve 266. The (second) hemostatic valve 266 seals a proximal opening of the extension device 260. In some implementations, one or more surgical implements can be inserted through the proximal opening/hemostatic valve 266. In some implementations of the extension device 260, the branching tube 276 of the extension device 260 constitutes a part of the arterial flow tubing 102 to allow the blood flow from the extension device 260 to the flow controller 300 (shown in FIG. 1). In some implementations of the extension device 260, the branching tube 276 of the extension device 260 can be a separate tube configured to fluidically connect (e.g., removably connect) with the arterial flow tubing 102 to allow the blood flow from the extension device 260 to the flow controller 300.

Referring to FIG. 2G, a perspective view of an exemplary implementation of an arterial connector 274 of the arterial access device 200 is shown. The arterial connector 274 is configured to connect the arterial sheath 220 with the extension device 260 such that the (first) lumen 226 of the arterial sheath 220, the defeater lumen 272, and the lumen 264 of the extension device 260 form a continuous lumen of the arterial access device 200. In the implementation of FIG. 2E, the arterial connector 270 comprises the (second) lock portion 268 of extension device 260 and the defeater 270. In this implementation, the defeater 270 comprises a proximal portion 270*a* and a distal portion 270*b*, wherein the distal portion 270*b* of the defeater 270 is configured to fill the lock lumen 236 of the (first) lock portion 238 of the arterial sheath 220 and extend through the (first) hemostatic valve 234. In an implementation, the distal portion 270*b* of the defeater 270 extends into the (first) lumen 226 of the arterial sheath 220.

In some implementations, the proximal portion 270*a* and the distal portion 270*b* of the defeater 270 have different diameters. In some implementations, the diameter of the proximal portion 270*a* is greater than the diameter of the distal portion 270*b*. In some implementations, the defeater

270 has at least one portion configured to fill the lock lumen 236. In the example implementations presented in FIGS. 2A-2G, the defeater 270 further comprises a frustoconical portion configured to fit the frustoconical portion of the lock lumen 236 and pierce the (first) hemostatic valve 234 of the arterial sheath 220. In some implementations, the distal portion 270*b* of the defeater 270 is configured to pierce the first hemostatic valve 234 of the arterial sheath 220. In some implementations, the frustoconical portion of the defeater 270 is disposed between the proximal 270*a* portion and distal portion 270*b* of the defeater 270. In some implementations, the at least one portion of the defeater 270 configured to fill the lock lumen 236 and/or the lock lumen 236 can have a shape selected from a group including straight, curved, cylindrical, conical, circular, spherical, hemispherical, or a combination of at least two shapes.

In the implementation of FIG. 2G, the (second) lock portion 268 of the extension device 260 further includes a slider mechanism 278 configured to releasably connect the lock portion of the extension device 260 with the lock portion 268 of the arterial sheath 220 when the distal portion 270*b* of the defeater 270 is fit into the lock lumen 236 of the arterial sheath 220. The slider mechanism 278 is configured to prevent or reduce any leakage when the defeater 270 pierces the hemostatic valve 234 of the arterial sheath 220. In some implementations, the slider mechanism 278 is a quick connect socket 281 configured to connect with an O-ring disposed on/in the lock portion 268 of the arterial sheath 220. In some implementations, the slider mechanism 278 is a bolt with internal threads configured to tighten around corresponding groves on the lock portion 268 of the arterial sheath 220. The slider mechanism 278 can be configured such that the locking mechanism can be operated singlehandedly.

Figure 2H:
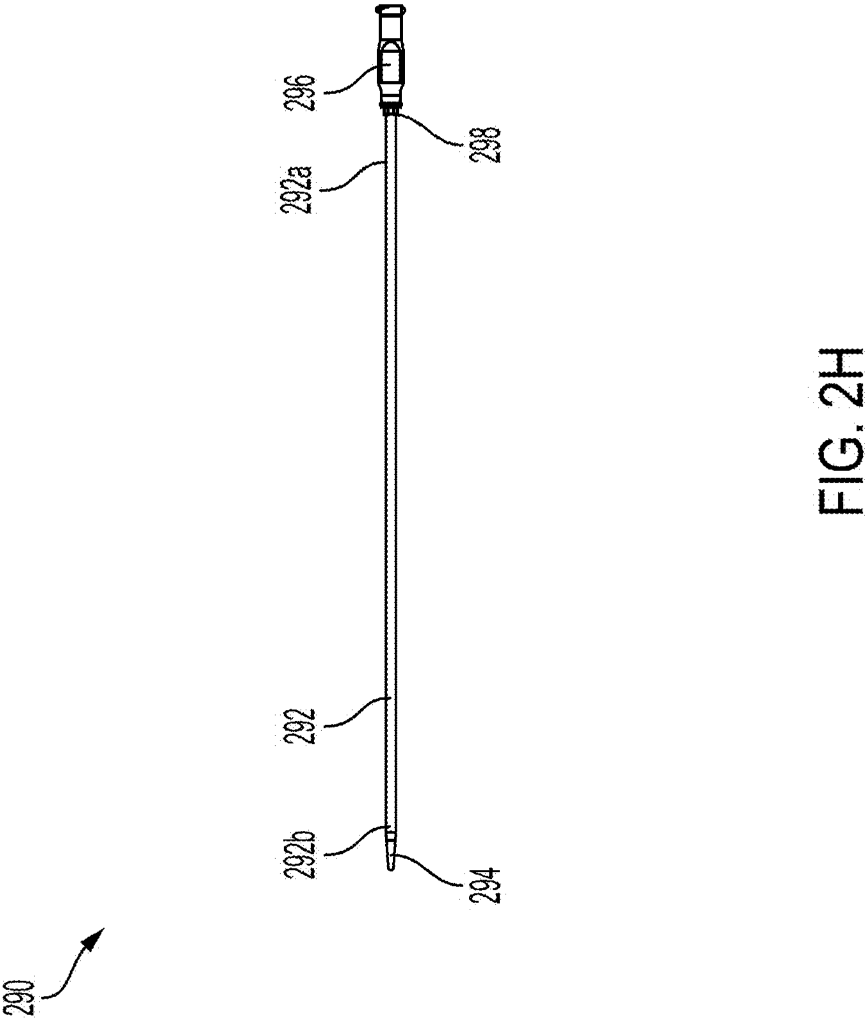
FIG. 2H shows a side view of an exemplary implementation of an arterial dilator of a TCAR system as described in this specification.

Referring to FIG. 2H, a side view of an exemplary implementation of an arterial dilator 290 of a TCAR system 100 is shown. The arterial dilator 290 shown in FIG. 2H is configured to traverse through the inner tube 224 of the arterial sheath 220, e.g., to make and/or enlarge an incision in the carotid artery for the inner tube 224 to enter the carotid artery. The arterial dilator 290 includes an arterial dilator extrusion 292, comprising a proximal end 292*a* and a distal end 292*b*, coupled to an arterial dilator hub 296 via an arterial dilator hub connector 298 at the proximal end 292*a* of the arterial dilator extrusion 292. The distal end 292*b* of the arterial dilator extrusion includes an incision tip 294 configured to make the incision in the artery for the inner tube 224 to enter the artery. A diameter of the arterial dilator hub 296 can be configured to be larger than a diameter of the inner tube 224 of the arterial sheath 220 to limit the travel of the arterial dilator extrusion 292 through the inner tube 224. In some implementations, the arterial dilator extrusion 292 can be secured to the arterial dilator hub 296 via an adhesive within the arterial dilator hub connector 298.

Figures 3A, 3B:
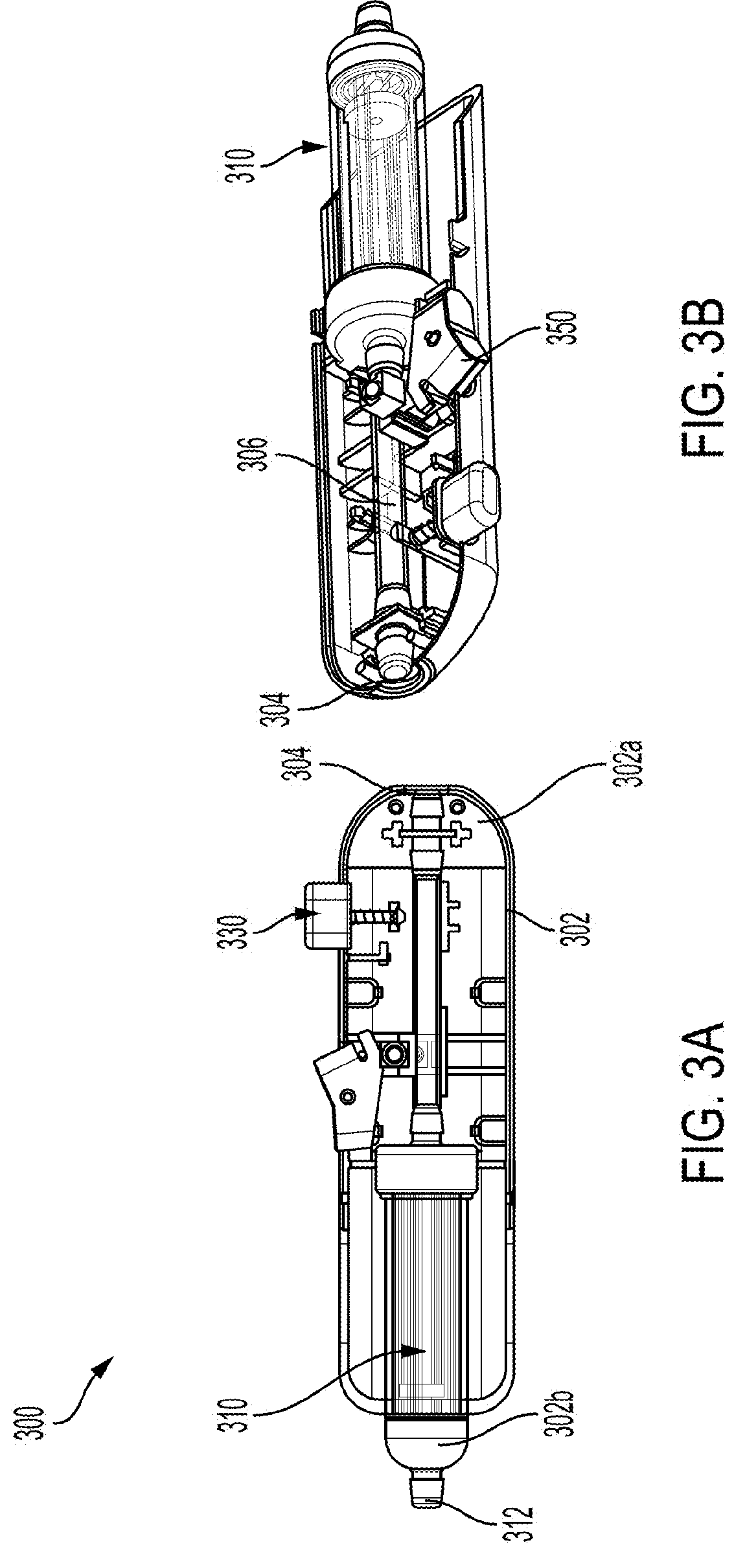
FIG. 3A shows cross-sectional side view of an exemplary implementation of a flow controller of a TCAR system as described in this specification.
FIG. 3B shows cross-sectional perspective view of an exemplary implementation of a flow controller of a TCAR system as described in this specification.

Referring to FIGS. 3A and 3B, cross-sectional views of an exemplary implementation of a flow controller 300 of a TCAR system 100 are shown. The flow controller 300 is configured to fluidically connect the arterial access device 200 and the venous sheath 400 (refer to FIG. 1) and control the rate of retrograde blood flow from the arterial access device 200 to the venous sheath 400. The flow controller 300 also includes a means for filtering the blood flowing from the arterial access device 200 into the venous sheath 400. The filtering allows for removal of plaque particle or other debris from the arterial blood. The implementation of the flow controller 300 presented in FIG. 3 includes a flow controller housing 302, an arterial flow tubing 102 connector disposed at a proximal end 302*a* of the flow controller 300, a flow controller lumen 306, a filter subassembly 310 configured to filter the blood, and a venous flow tubing connector 312 disposed at a distal end 302*b* of the flow controller 300. In an implementation, the flow controller 300 further includes a flow controller switch 350 and a flow restrictor 330 disposed on the flow controller housing 302 and can be configured to regulate the flow of blood between the arterial access device 200 and the venous sheath 400.

In some implementations, the flow controller 300 includes only the flow controller switch 350, but not the flow restrictor 330. In some implementations, the flow controller 300 includes only the flow restrictor 330, but not flow controller switch 350. In some implementations, the flow controller switch 350 is configured as a pivot with one end of the flow controller switch 350 pressing against the flow controller lumen 306. The flow controller switch 350 can be configured to restrict or completely block the flow of fluid through the flow controller lumen 306. The flow controller switch 350 can be configured to be operated (actuated) single-handedly (e.g., as a thumb-actuated switch). The flow controller switch 350 can also be configured to temporarily restrict flow, e.g., for as long as the switch actuated externally (pressed). In some implementations, the switch 350 allows the blood flow to be reduced/increase, e.g., to switch between "low" and "high" blood flow reversal.

Figure 3C:
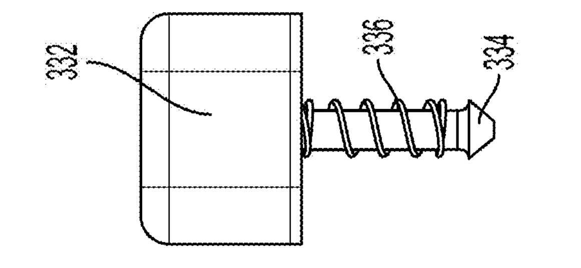
FIG. 3C shows a sideview of an exemplary implementation of a flow restrictor of a TCAR system as described in this specification.

Referring to FIG. 3C, a side view of an exemplary implementation of a flow restrictor 330 of the flow controller 300 is shown. The flow restrictor 330 is configured to control, limit, or completely interrupt the flow of blood (i.e., controlling flow rate and limiting blood loss while the TCAR system 100 is being connected) and also enable verification of flow reversal. In this implementation, the flow restrictor 330 comprises a button 332 mechanically coupled with a leg 334 and a compression spring 336 disposed on the leg 334. In this implementation, the leg 334 of the flow restrictor 330 is configured to restrict or completely block a diameter of the flow controller lumen 306 when a downward force is applied on to the button 332. In this implementation, when a downward force is applied onto the button 332, the compression spring 336 disposed on the leg 334 is compressed and the applied force is stored in the compression spring 336. When the downward force on the button 332 is removed, the compression spring 336 is decompressed and the restriction on the flow controller lumen 306 is removed by the upward movement of the button 332 and the leg 334 when the spring 336 is decompressed. In some implementations, the coils of the compression spring 336 can be selected to control a time of compression of the button 332/leg 334 on the flow controller lumen. In some implementations, the button 332/leg 334 is electrically connected to a controller to electrically control the time of restriction of the flow controller lumen 306 to control the flow rate of the blood through the flow controller 300.

In some alternative implementations, the flow controller 300 can include or can be fluidically connected to a pump and a controller electrically connected to the pump to regulate the retrograde flow of blood and the rate of blood flow through the flow controller 300. In some implementations, the flow controller 300 can further include flow sensor electrically connected to a controller mechanism, the flow sensor configured to measure a flow rate of the blood flow and ensure retrograde direction of the blood flow through the flow sensor, e.g., by actuating the controller mechanism, e.g., a pump or valve.

In the implementation of the flow controller 300 presented in FIGS. 3A-3B, the arterial flow tubing 304 connector of the flow controller 300 is configured to connect to the arterial flow tubing 102 including the (second) branching tube 276 of the extension device 260. In some implementations, the (second) branching tube 276 of the extension device 260 and the arterial flow tubing connector 304 are fluidically connected (e.g., removably connected) via the arterial flow tubing 102. In the implementation of the flow controller 300 presented in FIGS. 3A-3B, the venous flow tubing connector 312 of the flow controller 300 is configured to connect to a branching tube of the venous sheath 400 (presented in the paragraphs below). In some implementations, the branching tube of the venous sheath 400 and the venous flow tubing connector 312 are fluidically connected via the venous flow tubing 104 (as shown in FIG. 1).

Figure 3D:
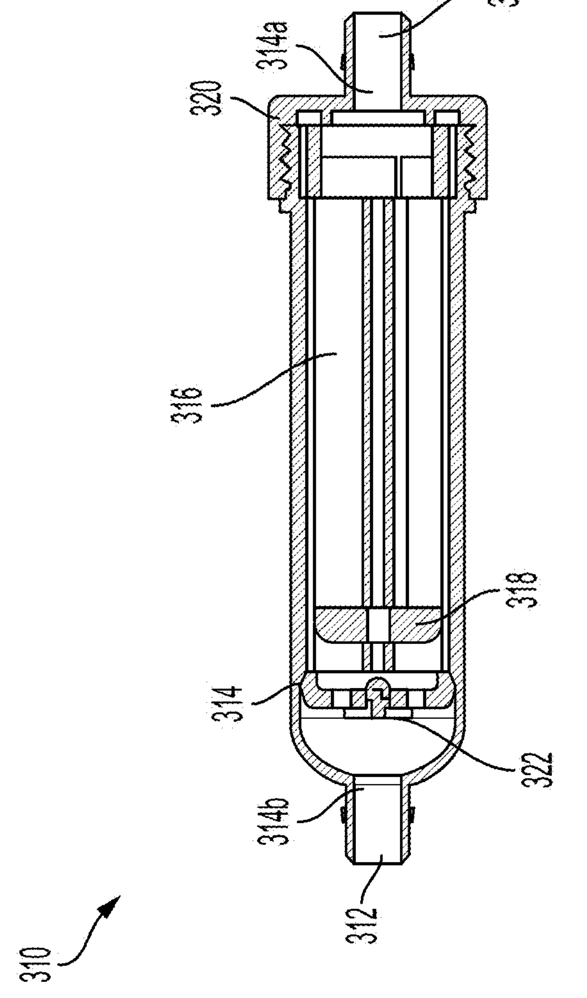
FIG. 3D shows a cross-sectional view of an exemplary implementation of a filter subassembly of a TCAR system as described in this specification.

Referring to FIG. 3D, a cross-sectional view of an exemplary implementation of a filter subassembly 310 of the flow controller 300 is shown. In this implementation, the filter subassembly 310 comprises a filter housing 314, a flow controller lumen connector 316 disposed at a proximal end 314*a* of the filter housing 314 and configured to fluidically connect with the flow controller lumen 306, a blood reservoir 316 to receive the blood from the flow controller lumen 306 via the flow controller lumen connector 316, a filter 318 disposed in the blood reservoir 316 and configured to filter the blood to remove any particles, and the venous flow tubing connector 312 to output the filtered blood to the venous sheath 400. In some implementations, the filter 318 can have a pore size of about 50 um to about 300 um, e.g., about 100 um to about 120 um. In this implementation, the filter subassembly 318 also includes a threaded filter cap 320 to seal the blood reservoir 316 and a check valve 322 configured to prevent backflow of blood from the venous flow tubing 104. In some implementations, the filter subassembly 310 is mounted in the flow controller 300 such that the filter subassembly 310 is removable from the flow controller 300 without tools.

Figure 4A:
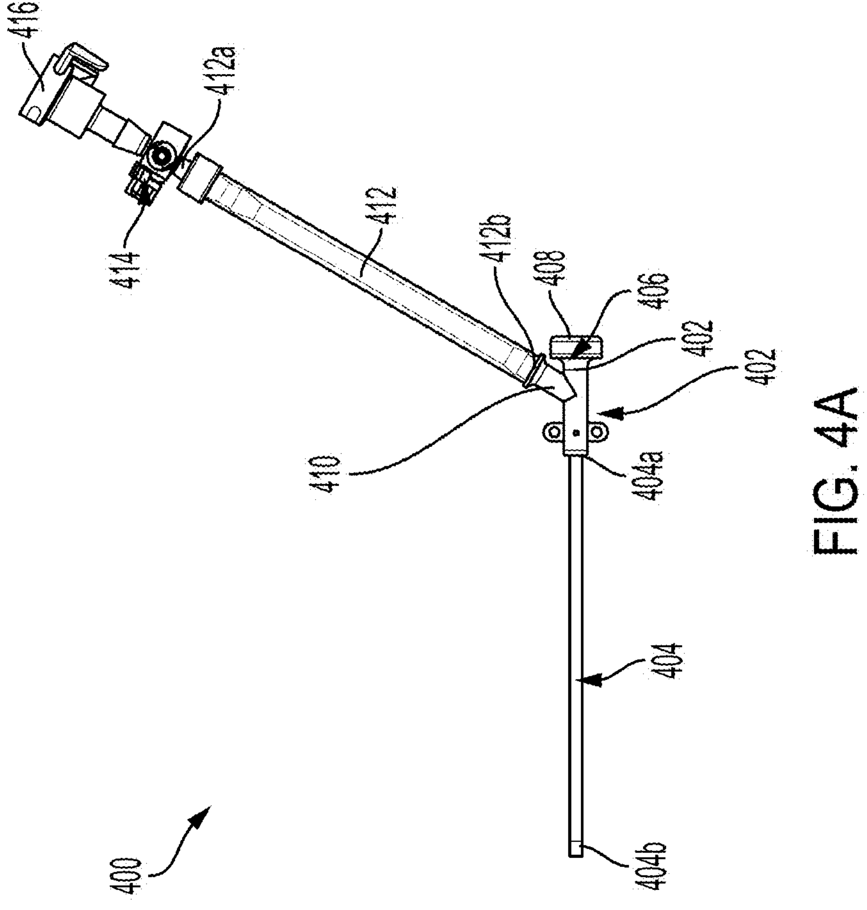
FIG. 4A shows a side view of an exemplary implementation of a venous sheath of a TCAR system as described in this specification.

Referring to FIG. 4A, a side view of an exemplary implementation of the venous sheath 400 of a TCAR system 100 is shown. The implementation of the venous sheath 400 presented in FIG. 4A includes a (third) body 402 comprising a proximal end 402*a*, a distal end 402*b*, a lumen (not shown in FIG. 4A), a (third) hemostatic valve 406 positioned at the proximal end 402*a*, and a hemostatic cap 408 coupled to the hemostatic valve 406. The hemostatic valve 406 can be configured to prevent leaking of the blood from the lumen and prevent air from entering the venous sheath 400 during the TCAR procedure. In some implementations, the hemostatic cap 408 can be removably connected to the hemostatic valve 406. The hemostatic valve 406 seals a proximal opening of the venous sheath 400. In some implementations, one or more surgical implements can be inserted through the proximal opening/hemostatic valve 406 of the venous sheath 400.

In some implementations of the venous sheath 400, the venous sheath 400 can further comprise an (second) inner tube 404, at least partially disposed in the body 402 of the venous sheath 400, forming a part of the lumen of the venous sheath 400. In this implementation, a distal end 404*b* of the inner tube 404 can be configured to be inserted into a vein and a proximal end 404*a* of the inner tube 404 can be connected to the lumen of the body 402 of the venous sheath 400. In some implementations, the venous sheath 400 is configured to be placed in the femoral vein to return the filtered blood back to the patient.

In some implementations of the venous sheath 400, such as the implementation presented in FIG. 4A, the venous sheath 400 can include a (third) branching tube 412 disposed on the body 402 of the venous sheath 400. In the implementation shown in FIG. 4A, the branching tube 412 comprises a proximal end 412*a* and a distal end 412*b* attached to the body 402 of the venous sheath 400. In this implementation, the distal end 412*b* of the branching tube 412 is connected to the body 402 of the venous sheath 400 such that a branching lumen (not shown in FIG. 4A) of the branching tube 412 is in fluid communication with the lumen of the venous sheath 400. In this implementation, the distal end 412*b* of the branching tube 412 forms a lateral opening 410 in the lumen of the venous sheath 400. In some implementations, the lateral opening 410 is positioned between the inner tube 404 and the hemostatic valve 406 of the venous sheath 400. In some implementations, the branching tube 412 of the venous sheath 400 can be configured to fluidically connect with the flow controller 300 via a flow controller connector 416 of a second stopcock valve subassembly 414, disposed on the proximal end 412*a* of the branching tube 412, to allow the blood flow from the flow controller 300 to the venous sheath 400. In some implementations, the flow controller connector 416 is fluidically connected to the flow controller 300 via the venous flow tubing 104 (as shown in FIG. 1). In some implementations, the flow controller connector 416 includes a connection mechanism similar to that of the arterial connector 274, e.g., a quick connect mechanism.

Figures 4B, 4C:
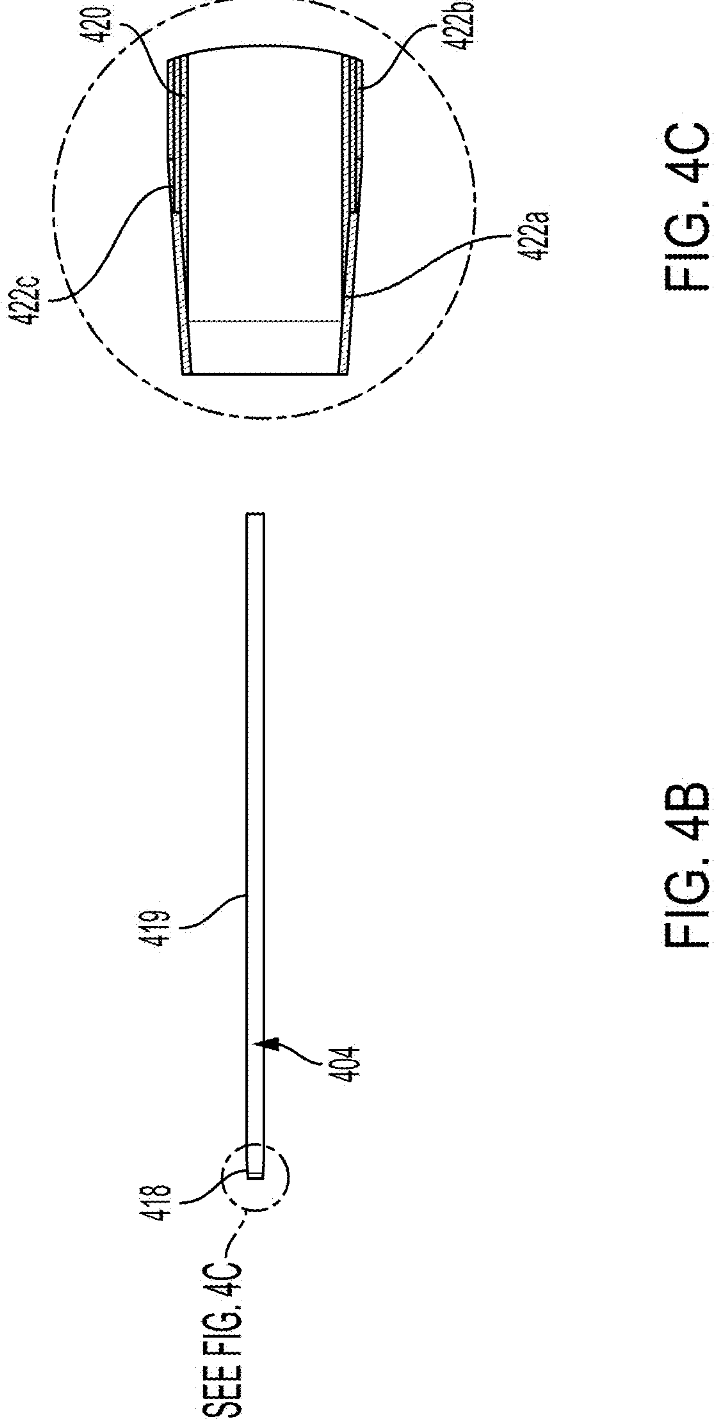
FIG. 4B shows a side view and the distal end of an exemplary implementation of an inner tube of the venous sheath presented in FIG. 4A.
FIG. 4C shows a cross-sectional view of the distal end of an exemplary implementation of an inner tube of the venous sheath presented in FIG. 4A.

Referring to the drawings, FIGS. 4B and 4C present a side view and a cross-sectional view of the distal end 404*b* of an exemplary implementation of an inner tube 404 of the venous sheath 400 presented in FIG. 4A. In the implementations presented in FIGS. 4B and 4C, the inner tube 404 of the venous sheath 400 comprises a liner 420 made of a polymer material, e.g., comprising polytetrafluoroethylene (PTFE), and extends from the proximal end 404*a* of the inner tube 404 to a point about 1-3 mm from the distal end 404*b* of the venous sheath 400. In some implementations, the inner tube 404 of the venous sheath 400 comprises a coiled wire 422*c* forming a layer around the liner. In some implementations, coiled wire 422*c* is made of a metal and extends from the proximal end 404*a* of the inner tube 404 to a point about 2-5 mm from the distal end 404*b*. The coiled wire 422*c* and/or liner 420 are coated with a polymer material. In an example segment D 418, as shown in FIGS. 4B and 4C, the liner 420 extends distally from a distal end of the coiled wire 422*c*. The coiled wire 422*c* and the liner 420 a coated with a fourth material forming a fourth layer 422*a*. In an example implementation, segment D 418 is between 2 and 8 mm, e.g., about 4-5 mm in length. In some implementations, the fourth layer 422 (alone) forms the distal-most tip of the distal end 404*b* of the inner tube 404. In an example segment E 419, proximal to segment D 418, as shown in FIGS. 4B and 4C, the coiled wire 422*c* is coated with a fifth material forming a fifth layer 422*b* contiguous with the fourth layer 422*a*. In an example implementation, segment E 419 is between about 100 and 140 mm, e.g., about 125 mm in length. In some implementations, the fourth material is a 63D Pebax, the fifth material is a 55D Pebax, and the coil material is a 0.004" coiled round wire.

Figure 4D:
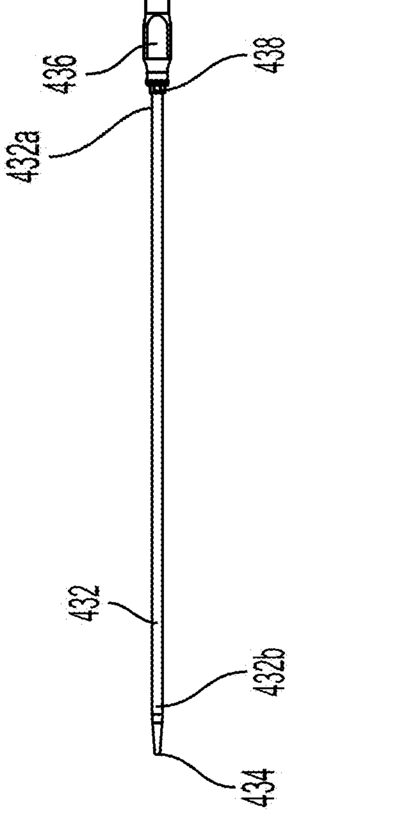
FIG. 4D shows a side view of an exemplary implementation of a venous dilator of a TCAR system as described in this specification.

Referring to FIG. 4D, a side view of an exemplary implementation of a venous dilator 430 of a TCAR system 100 is presented. The venous dilator 430 shown in FIG. 4D is configured to traverse through the inner tube 404 of the venous sheath 400 to make and/or enlarge an incision in the vein for the inner tube 404 to enter the vein. The venous dilator 430 includes a venous dilator extrusion 432, comprising a proximal end 432*a* and distal end 432*b*, coupled to a venous dilator hub 436 via a venous dilator hub connector 438 at the proximal end 432*a* of the venous dilator extrusion 432*a*. The distal end 432*b* of the venous dilator extrusion 432 includes an incision tip 434 configured to make the incision in the vein for the inner tube 404 to enter the vein. A diameter of the venous dilator hub 436 can be configured to be larger than a diameter of the inner tube 404 of the venous sheath 400 to limit the travel of the venous dilator extrusion 432 through the inner tube 404. In some implementations, the venous dilator extrusion 432 can be secured to the venous dilator hub 436 via an adhesive within the venous dilator hub connector 438.

Figure 5:
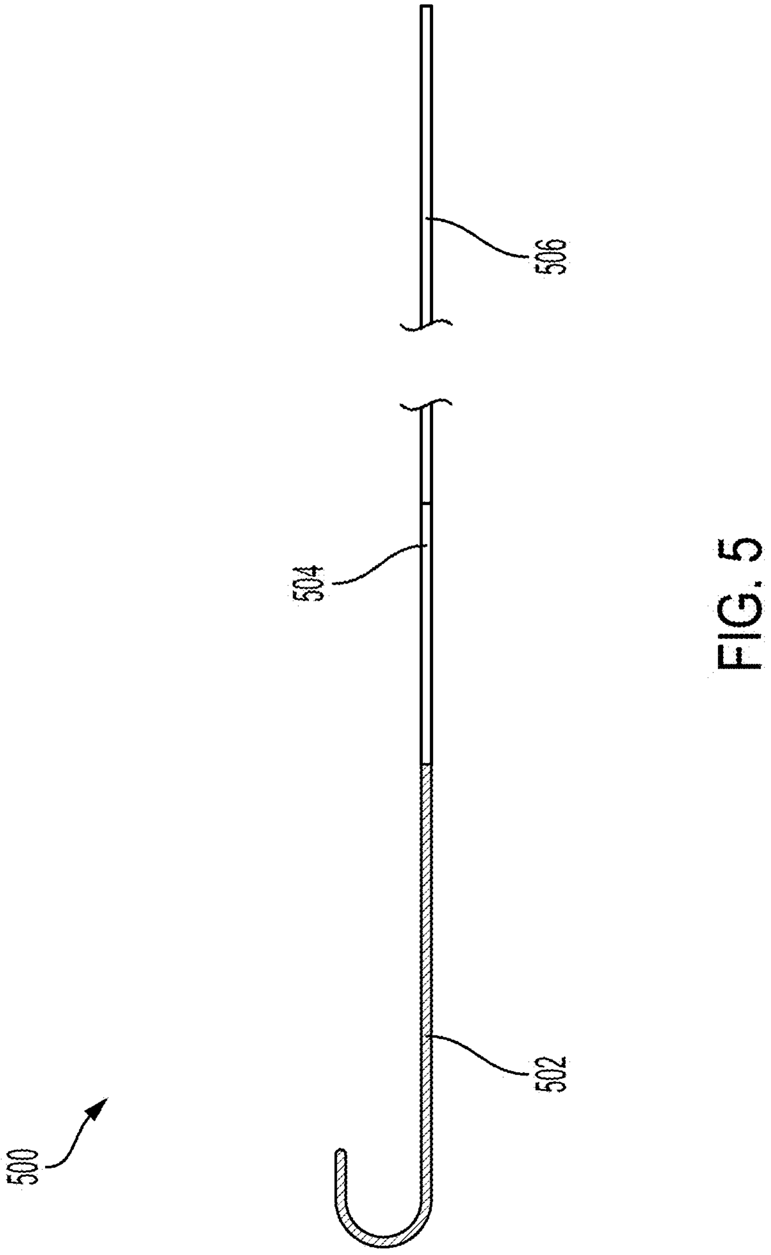
FIG. 5 shows a side view of an exemplary implementation of a guidewire of a TCAR system as described in this specification.

Referring to FIG. 5, a side view of an exemplary implementation of a guidewire 500 of a TCAR system 100 is shown. The guidewire 500 can be configured to traverse the inner tubes (224 and 404) of the arterial sheath 220 or the venous sheath 400 to deliver a device, e.g., a stent, to the artery or the vein respectively. The guidewire 500 presented in FIG. 5 can be composed of a first segment 502, second segment 504, and a third segment 506. In the implementation presented in FIG. 5, the first segment 502 is the most distal segment and is configured to be flexible compared to the second segment 504 which is configured to be stiff. In some implementations, the first segment 502 can include a (super-elastic) tapered Nitinol core with a rounded distal tip. The distal end can be configured as a deformable hook with a diameter of about 4-10 mm, e.g., 6 mm. In the first segment 502, a coiled metal wire is wound around the core. In some implementations, the first segment 502 is about 40-50 mm, e.g., about 50 mm long. The nitinol core extends through the second segment 504 and third segment 506. In some implementations, the second segment 504, which does not include the coiled wire, is about 10-40 mm, e.g., about 15 mm long. In the implementation presented in FIG. 5, the third segment 506 comprises a polymer coating. In some implementations, the coating can comprise polytetrafluoroethylene (PTFE). In some implementations, the third segment 506 is about 800-900 mm, e.g., about 830 mm long.

While the advantages and preferred embodiments of the present invention have been described hereinbefore, those skilled in the art should be understood that the above are merely several illustrative embodiments of the present invention without limiting the scope thereof, wherein various modifications, alterations or substitutions may be made to the specific components of the embodiments without departing from the spirit and scope of the invention and its claims.

What is claimed is:

1. A system for neuroprotection for use during carotid arterial interventions including transcarotid artery revascularization (TCAR), the system comprising:

an arterial access device comprising an arterial sheath having a distal and a proximal end, and an extension device removably connected to the proximal end of the arterial sheath, the arterial sheath comprising:

(a) a first body having a proximal end, a distal end, a first lumen, and a first hemostatic valve positioned at the proximal end, and (b) a second lock portion having a proximal end, a distal end, the second lock portion extending distally from the distal end of the second body, the second lock portion configured to releasably interlock with the first lock portion and (c) a defeater configured to pierce the first hemostatic valve and at least partially disposed inside the second body, the Defeater having a proximal end, a distal end, and a Defeater lumen extending distally from a distal end of the second lumen, the Defeater configured to actuate the first hemostatic valve such that, when the extension device is connected to the arterial sheath, the first lumen, the Defeater lumen, and the one lumen form a continuous lumen;

a venous sheath fluidly connected with the arterial access device, and wherein the distal end of the first body of the arterial sheath comprises a footplate configured to seal an insertion point in the carotid artery during the carotid arterial interventions.

2. The system of claim 1, wherein the arterial sheath comprises an inner tube at least partially disposed inside the first body, the inner tube forming a part of the first lumen, the inner tube having a proximal end and a distal end.

3. The system of claim 1, wherein the first body comprises a plurality of notches or fenestrations.

4. The system of claim 1, comprising a first branching tube having a proximal end, a distal end attached to the arterial sheath, and a first branching lumen in fluid communication with the first lumen, the first branching lumen having a proximal end and a distal end.

5. The system of claim 4, wherein the distal end of the first branching lumen forms a first lateral opening in the first lumen positioned between the proximal end of the inner tube and the first hemostatic valve.

6. The system of claim 1, wherein, when the extension device is connected to the arterial sheath, the first lock portion is at least partially disposed inside the second lock portion and the second lock portion comprises a slider mechanism configured to releasably lock the first lock portion to the second lock portion.

7. The system of claim 1, wherein the defeater has a frustoconical portion configured to at least partially fill a frustoconical portion of the lock lumen.

8. The system of claim 1, wherein the defeater has a cylindrical distal portion having a first diameter and a cylindrical proximal portion having a second diameter, wherein the second diameter is greater than the first diameter and the frustoconical portion of the defeater is disposed between the distal portion and the proximal portion of the defeater.

9. The system of claim 1, comprising a second branching tube having a proximal end, a distal end attached to the extension device, and a second branching lumen fluidically connected with the second lumen, the second branching lumen having a proximal end and a distal end.

10. The system of claim 9, wherein the distal end of the second branching lumen forms a second lateral opening in the second lumen positioned between the defeater and the second hemostatic valve.

11. The system of claim 9, comprising a flow controller having a proximal end, a distal end, and a lumen, the distal end of the flow controller being removably attached to the proximal end of the second branching tube, the lumen of the flow controller being fluidically connected with the first lumen and the second lumen.

12. The system of claim 1, wherein the venous sheath comprises:

(a) a third body having a proximal end, a distal end, a third lumen, and a third hemostatic valve positioned at the proximal end, and (b) a third branching tube having a proximal end, a distal end attached to the third body of the venous sheath, and a third branching lumen in fluid communication with the third lumen, the third branching lumen having a proximal end and a distal end removably attached to the proximal end of the flow controller, the lumen of the flow controller being fluidically connected with the third lumen.

13. The system of claim 2, wherein the distal end of the inner tube of the arterial sheath further comprises a flexible tip configured to bend in a bending angle between 0° and 30°.

14. The system of claim 2, wherein the inner tube of the arterial sheath comprises a liner forming an innermost layer of at least a part of the inner tube.

15. The system of claim 14, wherein the inner tube of the arterial sheath comprises a coiled wire forming a layer around the liner in at least a part of the inner tube, wherein the coiled wire, the liner, or both, are coated with a polymer material.

16. The system of claim 15, wherein the inner tube of the arterial sheath comprises a segment A, wherein the liner extends distally from the distal end of the coiled wire, and the coiled wire and the liner are coated with a first material forming a first layer.

17. The system of claim 14, wherein the inner tube of the arterial sheath comprises a segment B proximal to segment A, wherein the coiled wire is coated with a second material forming a second layer contiguous with the first layer.

18. The system of claim 17, wherein the inner tube of the arterial sheath comprises a segment C proximal to segment B, wherein the coiled wire is coated with a third material forming a third layer contiguous with the second layer, the third material stiffer than the first material and second material.

19. The system of claim 2, wherein the inner tube of the venous sheath comprises a liner forming an innermost layer of at least a part of the inner tube.

20. The system of claim 19, wherein the inner tube of the venous sheath comprises a coiled wire forming a layer around the liner in at least a part of the inner tube, wherein the coiled wire, the liner, or both, are coated with a polymer material.

21. The system of claim 20, wherein the inner tube of the venous sheath comprises a segment D, wherein the liner extends distally from the distal end of the coiled wire, and the coiled wire and the liner are coated with a fourth material forming a fourth layer.

22. The system of claim 20, wherein the inner tube of the venous sheath comprises a segment E proximal to segment D, wherein the coiled wire is coated with a fifth material forming a fifth layer contiguous with the fourth layer.

23. The system of claim 1, further comprising an arterial dilator configured to traverse through the inner tube of the arterial sheath to make or expand an incision in the carotid artery for the inner tube to enter the carotid artery.

24. The system of claim 23, wherein the arterial dilator comprises:

an arterial dilator extrusion comprising a proximal end and a distal end, wherein the distal end of the arterial dilator extrusion includes an incision tip configured to make the incision in the artery to for the inner tube to enter the artery; and an arterial dilator hub coupled to the proximal end of the arterial dilator extrusion via an arterial dilator hub connector.

25. The system of claim 1, further comprising a venous dilator configured to traverse through the inner tube of the venous sheath to make or expand an incision in a femoral vein for the inner tube to enter the femoral vein.

26. The system of claim 25, wherein the venous dilator comprises:

a venous dilator extrusion comprising a proximal end and a distal end, wherein the distal end of the venous dilator extrusion includes an incision tip configured to make the incision in the vein to for the inner tube to enter the vein; and a venous dilator hub coupled to the proximal end of the venous dilator extrusion via a venous dilator hub connector.

27. The system of claim 1, further comprising a guidewire configured to traverse the inner tube of the arterial sheath or the venous sheath and deliver a stent to the carotid artery or the femoral vein.

28. The system of claim 27, wherein the guidewire comprises a first segment and a second segment, the first segment configured as a deformable hook, the first segment being more flexible than the second segment, wherein the first segment comprises a Nitinol core and a coiled wire layer wound around the core.

* * * * *